United States Patent
Aryan (10) Patent No.: US 8,257,407 B2
(45) Date of Patent: Sep. 4, 2012

(54) BONE PLATE SYSTEM AND METHOD

(76) Inventor: Henry E. Aryan, Fresno, CA (US)

( * ) Notice: Subject to any disclaimer, the term of this patent is extended or adjusted under 35 U.S.C. 154(b) by 584 days.

(21) Appl. No.: 12/428,961

(22) Filed: Apr. 23, 2009

(65) Prior Publication Data

US 2009/0270925 A1 Oct. 29, 2009

Related U.S. Application Data

(60) Provisional application No. 61/125,320, filed on Apr. 23, 2008.

(51) Int. Cl.
*A61B 17/80* (2006.01)

(52) U.S. Cl. .................................................. 606/286

(58) Field of Classification Search ............... 606/246, 606/278, 279, 280, 71, 281–291, 300–306, 606/310–312, 86 R, 99
See application file for complete search history.

(56) References Cited

U.S. PATENT DOCUMENTS

| | | | | |
|---|---|---|---|---|
| 4,484,570 A * | 11/1984 | Sutter et al. | | 606/282 |
| 4,696,290 A * | 9/1987 | Steffee | | 606/286 |
| 5,092,866 A * | 3/1992 | Breard et al. | | 606/54 |
| 5,129,899 A * | 7/1992 | Small et al. | | 606/290 |
| 5,300,074 A * | 4/1994 | Frigg | | 606/67 |
| 5,498,263 A * | 3/1996 | DiNello et al. | | 606/292 |
| 5,569,251 A * | 10/1996 | Baker et al. | | 606/281 |
| 5,607,425 A * | 3/1997 | Rogozinski | | 606/264 |
| 5,613,967 A * | 3/1997 | Engelhardt et al. | | 606/305 |
| 5,674,296 A * | 10/1997 | Bryan et al. | | 623/17.16 |
| 5,676,666 A * | 10/1997 | Oxland et al. | | 606/86 B |
| 5,676,667 A * | 10/1997 | Hausman | | 606/281 |
| 5,713,900 A * | 2/1998 | Benzel et al. | | 606/250 |
| 5,954,722 A * | 9/1999 | Bono | | 606/281 |
| 6,102,951 A * | 8/2000 | Sutter et al. | | 623/18.11 |
| 6,120,503 A * | 9/2000 | Michelson | | 606/86 A |
| 6,235,028 B1 * | 5/2001 | Brumfield et al. | | 606/53 |
| 6,235,033 B1 * | 5/2001 | Brace et al. | | 606/288 |
| 6,296,647 B1 * | 10/2001 | Robioneck et al. | | 606/105 |
| 6,527,776 B1 * | 3/2003 | Michelson | | 606/70 |
| 6,551,319 B2 * | 4/2003 | Lieberman | | 623/17.11 |
| 6,554,830 B1 * | 4/2003 | Chappius | | 606/246 |
| 6,575,975 B2 * | 6/2003 | Brace et al. | | 606/86 B |
| 6,595,993 B2 * | 7/2003 | Donno et al. | | 606/71 |
| 6,599,290 B2 * | 7/2003 | Bailey et al. | | 606/86 B |
| 6,613,053 B1 * | 9/2003 | Collins et al. | | 606/293 |
| 6,623,486 B1 * | 9/2003 | Weaver et al. | | 606/281 |
| 6,669,729 B2 * | 12/2003 | Chin | | 623/17.11 |
| 6,764,489 B2 * | 7/2004 | Ferree | | 606/279 |
| 6,827,722 B1 * | 12/2004 | Schoenefeld | | 606/104 |
| 6,890,334 B2 * | 5/2005 | Brace et al. | | 606/281 |
| 6,893,444 B2 * | 5/2005 | Orbay | | 606/281 |
| 6,926,718 B1 * | 8/2005 | Michelson | | 606/247 |
| 6,955,677 B2 * | 10/2005 | Dahners | | 606/287 |
| 6,964,665 B2 * | 11/2005 | Thomas et al. | | 606/86 A |
| 6,969,390 B2 * | 11/2005 | Michelson | | 606/86 B |
| 7,052,499 B2 * | 5/2006 | Steger et al. | | 606/291 |
| 7,074,203 B1 * | 7/2006 | Johanson et al. | | 602/72 |
| 7,074,221 B2 * | 7/2006 | Michelson | | 606/70 |

(Continued)

*Primary Examiner* — Alvin Stewart (74) *Attorney, Agent, or Firm* — GSS Law Group (57) ABSTRACT

A system, components of the system, and methods for attaching a plate between two or more bones or bone fragments. The system includes distraction pins having a threaded bone attachment or screw section and a detachable shaft section. The screw section of the distraction pins remain in the bone and are used to affix a plate to the bones.

4 Claims, 6 Drawing Sheets

U.S. PATENT DOCUMENTS

| | | | |
|---|---|---|---|
| 7,175,624 B2* | 2/2007 | Konieczynski et al. | 606/71 |
| 7,338,493 B1* | 3/2008 | Vandewalle | 606/86 A |
| 7,354,442 B2* | 4/2008 | Sasso et al. | 606/280 |
| 7,416,553 B2* | 8/2008 | Patel et al. | 606/246 |
| 7,465,306 B2* | 12/2008 | Pond et al. | 606/86 A |
| 7,481,829 B2* | 1/2009 | Baynham et al. | 606/289 |
| 7,491,218 B2* | 2/2009 | Landry et al. | 606/246 |
| 7,520,879 B2* | 4/2009 | Justis et al. | 606/86 A |
| 7,537,596 B2* | 5/2009 | Jensen | 606/280 |
| 7,559,929 B2* | 7/2009 | Denti | 606/86 A |
| 7,563,274 B2* | 7/2009 | Justis et al. | 606/279 |
| 7,572,276 B2* | 8/2009 | Lim et al. | 606/246 |
| 7,585,299 B2* | 9/2009 | Rezach | 606/60 |
| 7,585,312 B2* | 9/2009 | Rawlins et al. | 606/246 |
| 7,588,588 B2* | 9/2009 | Spitler et al. | 606/246 |
| 7,591,836 B2* | 9/2009 | Dick et al. | 606/246 |
| 7,611,527 B2* | 11/2009 | Freid et al. | 606/279 |
| 7,625,381 B2* | 12/2009 | Michelson | 606/105 |
| 7,635,379 B2* | 12/2009 | Callahan et al. | 606/266 |
| 7,648,521 B2* | 1/2010 | Hestad | 606/246 |
| 7,651,502 B2* | 1/2010 | Jackson | 606/99 |
| 7,670,341 B2* | 3/2010 | Leyden et al. | 606/65 |
| 7,736,380 B2* | 6/2010 | Johnston et al. | 606/280 |
| 7,780,711 B2* | 8/2010 | Orbay et al. | 606/287 |
| 7,794,483 B2* | 9/2010 | Capanni | 606/306 |
| 7,846,163 B2* | 12/2010 | Fourcault et al. | 606/68 |
| 7,905,907 B2* | 3/2011 | Spitler et al. | 606/279 |
| 7,909,830 B2* | 3/2011 | Frigg et al. | 606/86 A |
| 7,909,858 B2* | 3/2011 | Gerlach et al. | 606/280 |
| 7,914,558 B2* | 3/2011 | Landry et al. | 606/246 |
| 7,927,360 B2* | 4/2011 | Pond, Jr. et al. | 606/265 |
| 7,935,137 B2* | 5/2011 | Gorhan et al. | 606/301 |
| 7,955,361 B2* | 6/2011 | Kitchens | 606/281 |
| 7,955,364 B2* | 6/2011 | Ziolo et al. | 606/308 |
| 7,967,826 B2* | 6/2011 | Colleran et al. | 606/99 |
| 7,981,142 B2* | 7/2011 | Konieczynski et al. | 606/290 |
| 7,985,223 B2* | 7/2011 | Khodadadyan-Klostermann et al. | 606/71 |
| 7,985,224 B2* | 7/2011 | Michelson | 606/71 |
| 7,988,714 B2* | 8/2011 | Puekert et al. | 606/291 |
| 8,002,798 B2* | 8/2011 | Chin et al. | 606/246 |
| 8,016,861 B2* | 9/2011 | Mitchell et al. | 606/264 |
| 8,025,677 B2* | 9/2011 | Freid et al. | 606/246 |
| 8,070,749 B2* | 12/2011 | Stern | 606/71 |
| 2002/0099378 A1* | 7/2002 | Michelson | 606/61 |
| 2002/0120273 A1* | 8/2002 | Needham et al. | 606/61 |
| 2002/0128654 A1* | 9/2002 | Steger et al. | 606/69 |
| 2002/0151899 A1* | 10/2002 | Bailey et al. | 606/69 |
| 2002/0169453 A1* | 11/2002 | Berger | 606/73 |
| 2003/0028193 A1* | 2/2003 | Weil et al. | 606/73 |
| 2003/0083660 A1* | 5/2003 | Orbay | 606/69 |
| 2003/0135210 A1* | 7/2003 | Dixon et al. | 606/61 |
| 2003/0139811 A1* | 7/2003 | Watson et al. | 623/11.11 |
| 2003/0171754 A1* | 9/2003 | Del Medico | 606/69 |
| 2003/0199876 A1* | 10/2003 | Brace et al. | 606/69 |
| 2003/0208204 A1* | 11/2003 | Bailey et al. | 606/69 |
| 2004/0034353 A1* | 2/2004 | Michelson | 606/61 |
| 2004/0087951 A1* | 5/2004 | Khalili | 606/69 |
| 2004/0102780 A1* | 5/2004 | West, Jr. | 606/73 |
| 2004/0122431 A1* | 6/2004 | Biedermann et al. | 606/73 |
| 2004/0127897 A1* | 7/2004 | Freid et al. | 606/61 |
| 2004/0127899 A1* | 7/2004 | Konieczynski et al. | 606/69 |
| 2004/0127900 A1* | 7/2004 | Konieczynski et al. | 606/69 |
| 2004/0133207 A1* | 7/2004 | Abdou | 606/73 |
| 2004/0176766 A1* | 9/2004 | Shluzas | 606/65 |
| 2004/0177847 A1* | 9/2004 | Foley et al. | 128/95.1 |
| 2004/0210217 A1* | 10/2004 | Baynham et al. | 606/61 |
| 2004/0215190 A1* | 10/2004 | Nguyen et al. | 606/61 |
| 2004/0225290 A1* | 11/2004 | Ferree | 606/61 |
| 2004/0236335 A1* | 11/2004 | Michelson | 606/69 |
| 2005/0033299 A1* | 2/2005 | Shluzas | 606/61 |
| 2005/0107796 A1* | 5/2005 | Gerlach et al. | 606/69 |
| 2005/0149031 A1* | 7/2005 | Ciccone et al. | 606/73 |
| 2005/0165400 A1* | 7/2005 | Fernandez | 606/69 |
| 2005/0171540 A1* | 8/2005 | Lim et al. | 606/61 |
| 2005/0182404 A1* | 8/2005 | Lauryssen et al. | 606/69 |
| 2005/0273105 A1* | 12/2005 | Konieczynski et al. | 606/69 |
| 2006/0116678 A1* | 6/2006 | Impellizzeri | 606/69 |
| 2006/0122607 A1* | 6/2006 | Kolb | 606/71 |
| 2006/0149252 A1* | 7/2006 | Markworth et al. | 606/69 |
| 2006/0161158 A1* | 7/2006 | Orbay et al. | 606/69 |
| 2006/0167456 A1* | 7/2006 | Johnston et al. | 606/69 |
| 2006/0200147 A1* | 9/2006 | Ensign et al. | 606/69 |
| 2006/0241622 A1* | 10/2006 | Zergiebel | 606/73 |
| 2006/0264936 A1* | 11/2006 | Partin et al. | 606/61 |
| 2006/0264946 A1* | 11/2006 | Young | 606/69 |
| 2006/0271052 A1* | 11/2006 | Stern | 606/69 |
| 2006/0276794 A1* | 12/2006 | Stern | 606/69 |
| 2007/0010820 A1* | 1/2007 | Contiliano et al. | 606/73 |
| 2007/0250064 A1* | 10/2007 | Darois et al. | 606/73 |
| 2008/0097444 A1* | 4/2008 | Erickson et al. | 606/69 |
| 2008/0132960 A1* | 6/2008 | Weaver et al. | 606/308 |
| 2008/0140130 A1* | 6/2008 | Chan et al. | 606/280 |
| 2008/0140132 A1* | 6/2008 | Perez-Cruet | 606/301 |
| 2008/0161860 A1* | 7/2008 | Ahrens et al. | 606/280 |
| 2008/0195157 A1* | 8/2008 | Orschler et al. | 606/280 |
| 2008/0234752 A1* | 9/2008 | Dahners | 606/291 |
| 2008/0255559 A1* | 10/2008 | Leyden et al. | 606/62 |
| 2008/0255567 A1* | 10/2008 | Accordino | 606/90 |
| 2008/0288001 A1* | 11/2008 | Cawley et al. | 606/295 |
| 2008/0306550 A1* | 12/2008 | Matityahu | 606/290 |
| 2009/0036932 A1* | 2/2009 | Rouyer et al. | 606/280 |
| 2009/0076553 A1* | 3/2009 | Wolter | 606/280 |
| 2009/0076556 A1* | 3/2009 | McGarity et al. | 606/281 |
| 2009/0088805 A1* | 4/2009 | Leyden et al. | 606/280 |
| 2009/0088807 A1* | 4/2009 | Castaneda et al. | 606/286 |
| 2009/0105755 A1* | 4/2009 | Capote | 606/246 |
| 2009/0118773 A1* | 5/2009 | James et al. | 606/308 |
| 2009/0138051 A1* | 5/2009 | Olms et al. | 606/280 |
| 2009/0143824 A1* | 6/2009 | Austin et al. | 606/280 |
| 2009/0157121 A1* | 6/2009 | Harris et al. | 606/280 |
| 2009/0192553 A1* | 7/2009 | Maguire et al. | 606/305 |
| 2009/0264886 A1* | 10/2009 | Stern | 606/70 |
| 2009/0292318 A1* | 11/2009 | White et al. | 606/281 |
| 2009/0306724 A1* | 12/2009 | Leither et al. | 606/289 |
| 2010/0057086 A1* | 3/2010 | Price et al. | 606/70 |
| 2010/0076498 A1* | 3/2010 | Tyber et al. | 606/302 |
| 2010/0094356 A1* | 4/2010 | Varela et al. | 606/304 |
| 2010/0094357 A1* | 4/2010 | Wallenstein et al. | 606/309 |
| 2010/0106196 A1* | 4/2010 | Erickson et al. | 606/281 |
| 2010/0106199 A1* | 4/2010 | Sawa et al. | 606/304 |
| 2010/0114174 A1* | 5/2010 | Jones et al. | 606/279 |
| 2010/0131016 A1* | 5/2010 | Gerber et al. | 606/304 |
| 2010/0174323 A1* | 7/2010 | Fourcault et al. | 606/304 |
| 2010/0179600 A1* | 7/2010 | Steger et al. | 606/281 |
| 2010/0185246 A1* | 7/2010 | Castaneda et al. | 606/305 |
| 2010/0234897 A1* | 9/2010 | Fisher et al. | 606/286 |
| 2010/0262193 A1* | 10/2010 | Frigg et al. | 606/281 |
| 2010/0298887 A1* | 11/2010 | Jordan et al. | 606/304 |
| 2010/0331895 A1* | 12/2010 | Linke | 606/304 |
| 2011/0060373 A1* | 3/2011 | Russell et al. | 606/304 |
| 2011/0093020 A1* | 4/2011 | Wu | 606/304 |
| 2011/0097377 A1* | 4/2011 | Serhan et al. | 424/423 |
| 2011/0106172 A1* | 5/2011 | Wallenstein et al. | 606/286 |
| 2011/0213423 A1* | 9/2011 | Biedermann et al. | 606/304 |
| 2012/0041489 A1* | 2/2012 | Stern | 606/246 |
| 2012/0158066 A1* | 6/2012 | Freese | 606/279 |

* cited by examiner

BONE PLATE SYSTEM AND METHOD

CROSS REFERENCE TO RELATED APPLICATION

This application claims the benefit of the filing date of provisional patent application Ser. No. 61/125,320 filed Apr. 23, 2008.

FIELD

The present invention relates to devices used in surgeries for positioning and immobilizing bones.

BACKGROUND

Bone fixation devices are useful for promoting the healing of injured or damaged vertebral bone segments caused by trauma, bone spur growth, tumor growth, or degenerative disc disease. These devices immobilize the bone segments to ensure the proper growth of new osseous tissue between the damaged segments.

Available systems and devices used on the cervical spine possess several shortcomings in both design and implantation protocols or methods. For example, distraction screws are used during disc removal and subsequent bone work and these screws are removed prior to bone plate placement. The empty bone holes created by removal of the distraction screws can interfere with proper placement of the bone screws used to anchor the plate and can lead to poor plate alignment along the long axis of the spine. This is especially problematic since the surgical steps that precede plate placement may distort the anatomical landmarks required to ensure proper plate alignment, leaving the surgeon with little guidance during plate implantation. For these reasons, bone plates are frequently placed "crooked" in the vertical plane. Correct plate placement in the vertical plane is especially important in plates intended to accommodate subsidence, since the plate preferentially permits movement along its long axis. Thus, when the vertical axis of the plate and that of the spine are not properly aligned, the plate will further worsen the alignment as the vertebral bones subside.

The empty bone holes left by the removal of the distraction screws also act as stress concentration points on the vertebral bodies, and may cause the bone to fracture. Improper plate placement and bone fractures can significantly increase the likelihood of failure and lead to severe chronic pain, neurological injury, and the need for surgical revision with a second procedure.

In view of the proceeding, it would be desirable to design an improved bone plating system and placement method. The new device should provide ease of use, reliable bone fixation, and the design should also maximize the likelihood of proper plate placement and avoid steps that weaken the vertebral bodies.

SUMMARY

The present invention is directed to skeletal plating systems, components thereof, and methods of implant placement. These systems are used to adjust, align and maintain the spatial relationship of adjacent bones or bony fragments during healing and fusion after surgical reconstruction of skeletal segments. Embodiments of the invention are particularly suited for use in procedures to fuse vertebrae, but are not limited to such use.

Systems of the invention include one or more distraction pins having an upper detachable shaft and a lower screw section. The screw section may include a self tapping point, a threaded shank, and a head. The system also includes a plate that can be slid over the shaft sections of the distraction pins before the shafts are removed. This assures accurate positioning of the plate. The system further includes locking screws that are coupled to the heads of the screw sections of the distraction pins holding the plate in position. The locking screws may engage the plate in a fixed or dynamic implantation. The screw sections of the distraction pins can be driven into the bone by using a tool configured for the purpose, such as a screw driver, or in alternate embodiments, the shaft of the distraction pin may be used to drive the screw section. The screws may include apertures and a central bore to allow boney ingrowth into the screws.

Methods of the invention include the steps: placing a first and second distraction pin in a first and second bone segment body (the distraction pins having an upper section and a screw section); acting on the distraction pins to position the first and second vertebrae; sliding a plate over the distraction pins; removing the upper section or shaft of the distraction pins; and connecting a locking element to each screw section of the first and second distraction pins. In this way, the plate is held in position by locking elements and the screw sections of the distraction pin. The method may further comprise a step following sliding the plate over the distraction pins of further driving the screw sections into the bone segment. The forces applied to the screw sections during distraction may cause them to become loose, and driving the screws further into the bone before applying the plate may give the screw sections a fresh grip on the bone.

FIGURES

The invention may be more fully understood from the following detailed description taken in conjunction with the accompanying drawings, in which:

FIGS. 2a through 2f show a number of example screw section embodiments. FIGS. 2a-2c show cutaway side views of several example screw embodiments, while

DETAILED DESCRIPTION

The present invention is directed to skeletal plating systems, components thereof, and methods of implant placement. These systems are used to adjust, align and maintain the spatial relationship of adjacent bones or bony fragments during healing and fusion after surgical reconstruction of skeletal segments. Embodiments of the invention are particularly suited for use in procedures to fuse vertebrae, and examples discussed below will focus on such use. However, the invention is not limited to use on only on the spine.

Figure 1:
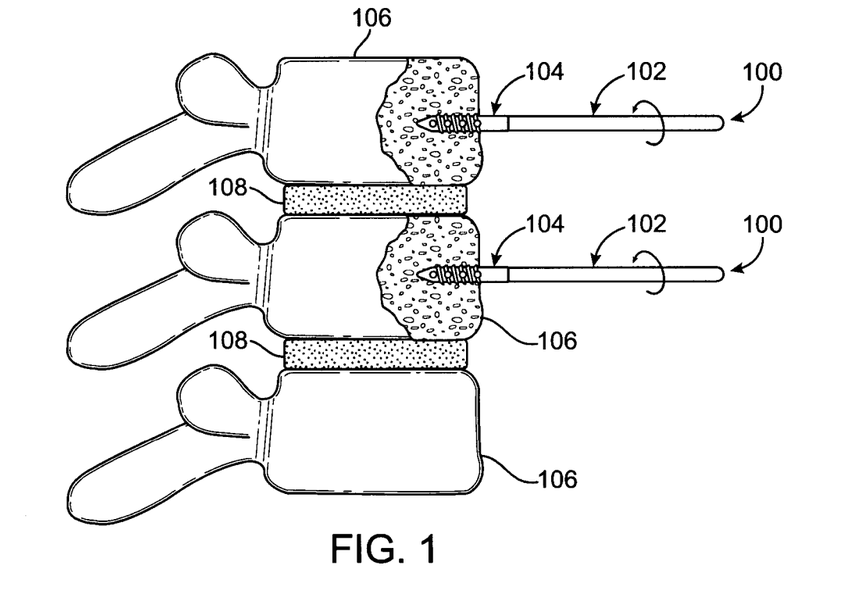
FIG. 1 shows a side view of two example distraction pins built in accord with the invention coupled to two vertebrae.

Referring to FIG. 1, two example distraction pins 100 built in accord with the invention may be seen coupled to adjacent vertebrae 106. The distraction pins 100 include a threaded bone attachment section or screw section 104 and a shaft 102 which are configured to be detachably coupled together. In the embodiment seen generally in FIGS. 1 through 6, the screw section 104 and the shaft 102 are threadably coupled together, but in alternate embodiments, other means for coupling could be used. In some methods of the invention the distraction pins 100 are inserted ½ to ¾ of the length of the screw section 104 to allow the screw section 104 to later be advanced further into the bone. Distraction is a term for spreading adjacent vertebrae apart so that procedures may be performed on the space between the vertebrae, such as a discectomy.

The size and length of the distraction pins 100 will be selected by the surgeon. The shaft 102 is typically configured with a length sufficient to extend outside the surgical site so that the distraction pin 100 can be manipulated as necessary for the procedure being performed. The shaft 102 of the distraction pin 100 is shown as being straight and cylindrical in cross section, but in alternate embodiments, many other shapes could be used. For example, the shaft 102 could have virtually any practical diameter or width, and shape in cross section. In the embodiments shown the shaft 102 is smooth, but in alternate embodiments the shaft 102 section may also include texture or other known means for enhancing the gripping of the shaft 102 either manually or by other instrumentation such as the distractor seen in FIG. 3. The shaft 102 may be constructed using any acceptable material or materials having sufficient strength for the intended use.

Figure 2A:
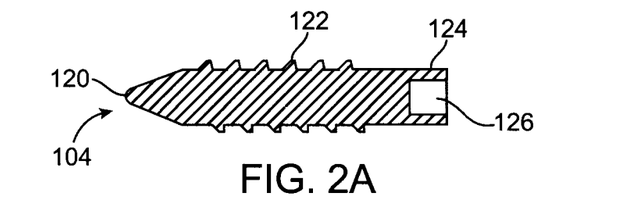
Figure 2B:
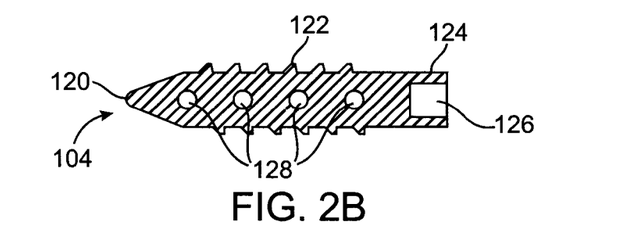
Figure 2C:
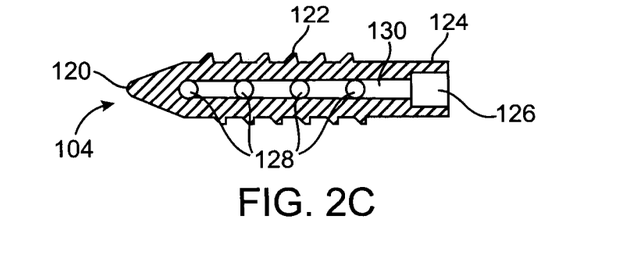

Example embodiments of the screw section 104 of the distraction pin 100 may be seen in FIGS. 2a through 2f. Referring to FIGS. 2a through 2c, all embodiments preferably include a self taping point 120, a threaded shank 122, and a head 126. In alternate embodiments, other configurations may be acceptable. The thread width, pitch, and other parameters of the shank 122 are preferably selected to provide a good grip when screwed into a bone. Embodiments of the screw section 104 seen in most of the Figures, but particularly in FIGS. 2b and 2c, include apertures to allow boney ingrowth into the screw section 104. Such growth will tend to inhibit the screws 104 from backing out or becoming loose. The apertures may be virtually any configuration. In FIG. 2b the screw section 104 includes side thru-holes 128 extending generally laterally through the screw section 104. FIG. 2c shows an embodiment of the screw section 104 including both a central bore 130 and side holes 128.

Figure 2D:
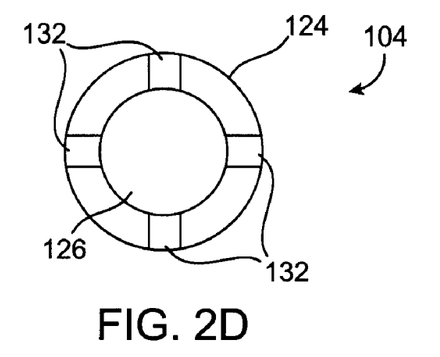
FIGS. 2d-2f show details of the head portion of several example screw section embodiments.
Figure 2E:
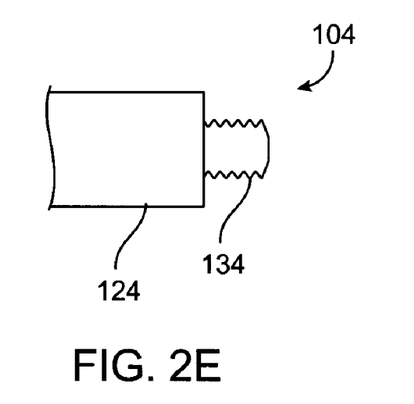
Figure 2F:
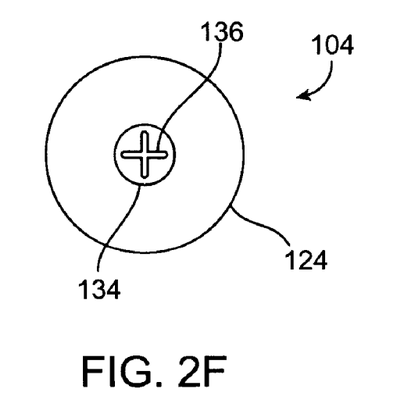

The head 124 of the screw section 104 is configured to couple to the shaft 102 of the distraction pin 100, and in some embodiments also to engage a tool configured for driving the screw section 104 into the bone. Any design for engaging a tool may be used. For example, FIG. 2d shows an end view of an example configuration of the head 124 of screw section 104 of FIG. 2a having slots 132 to engage a cross shaped tool such as a Phillips head screwdriver. An example alternate embodiment of the head 124 of screw section 104 can be seen in FIG. 2e having a screw end 134 to be screwed into an end of the shaft 102. This is a reversal of the coupling used in previously described embodiments. FIG. 2f shows an end view of the head 124 of screw section 104 of FIG. 2e with a cross shaped recess 136 in screw end 134 for engaging a Phillips head screwdriver. In alternate embodiments the head 124 may have a hexagonal socket or virtually any other practical means for engaging a tool for driving the screw section 104. The screw section 104 may be constructed from any acceptable biologically compatible material or materials having sufficient strength for the intended use including but not limited to stainless steel, titanium, various alloys and plastics, some resins, and ceramics. The screw section 104 may also include biologically active coatings that provide desired benefits such as enhancing bone growth or the like.

Figure 3:
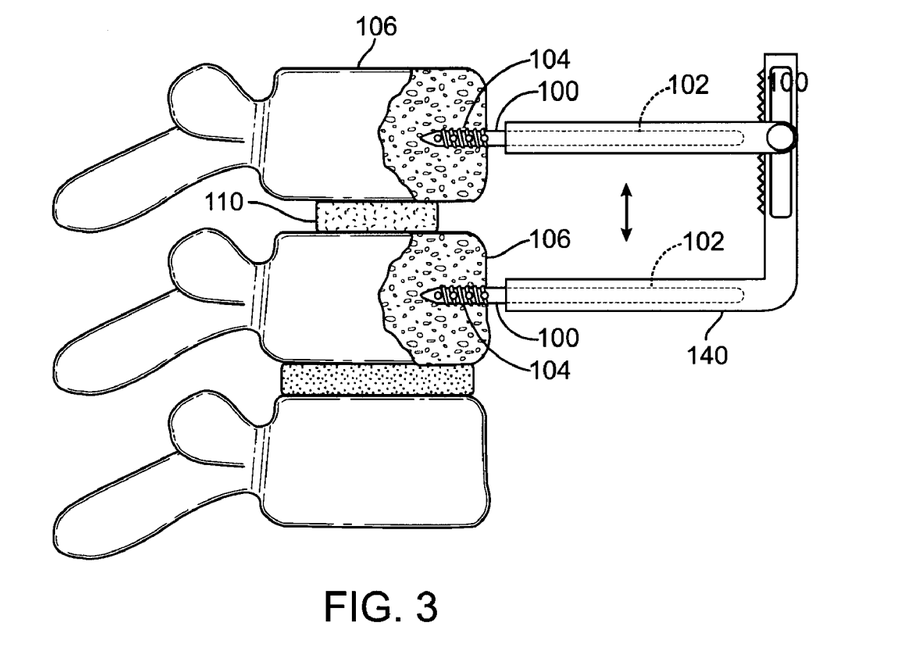
FIG. 3 shows a side view of a distractor acting on the distraction pins to separate the adjacent vertebrae.

FIG. 3 shows an example distractor acting on the distraction pins 100 by grasping the shaft 102 of the distraction pins 100, however, any method for applying force to the distraction pins 100 to position the bones to which the distraction pins 100 are attached may be used. In FIG. 3 the distraction pins 100 are coupled to vertebrae 106, and it is preferred that one distraction pin 100 per vertebra 106 is used, however in alternate embodiments, two or more distraction pins 100 could be used. Each distraction pin 100 is preferably installed along a center line of the vertebra. However, in alternate embodiments, especially those using more than one pin per vertebra, pins may be implanted in other locations. In a typical cervical fusion procedure, the disc is removed and replaced by a spacer 110 such as a bone fragment and or cage to maintain proper spacing between the adjacent vertebrae.

Figure 4:
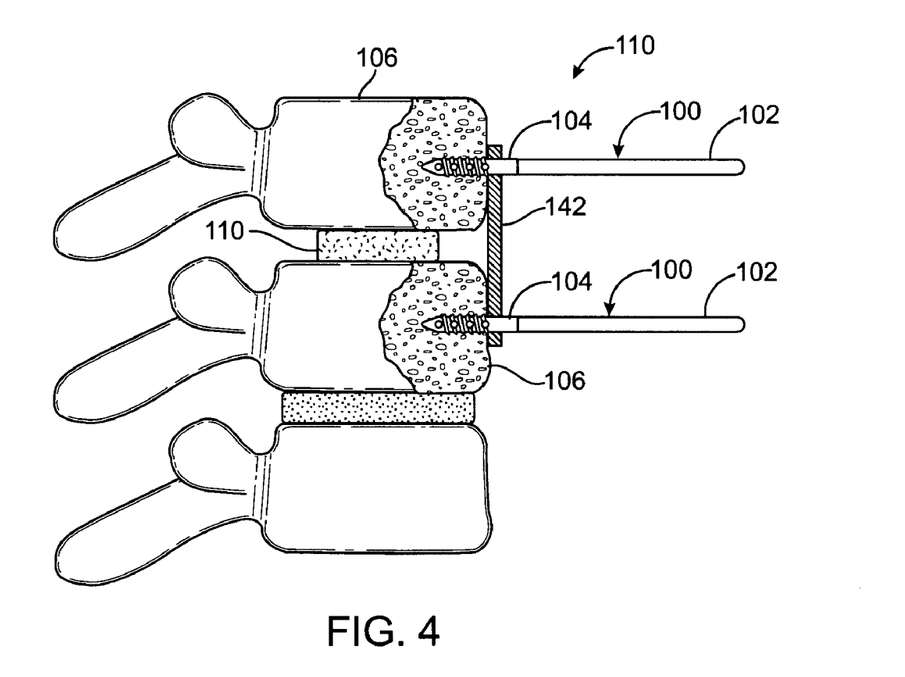
FIG. 4 shows an example plate slid over the distraction pins.

FIG. 4 shows the main elements of one example embodiment of the system 112 of the invention. A plate 142 is positioned over the distraction pins 100. Since distraction pins 100 are placed early in the surgical procedure while surgical landmarks are still intact, the likelihood of correct placement is high. The shafts 102 of the distraction pins 100 accurately guide the plate 142 into the desired position. And, because the screw section 104 of the distraction pins 100 will remain in place, likelihood of correct alignment of the plate 142 attached to the screws 104 is therefore also improved.

Figure 5:
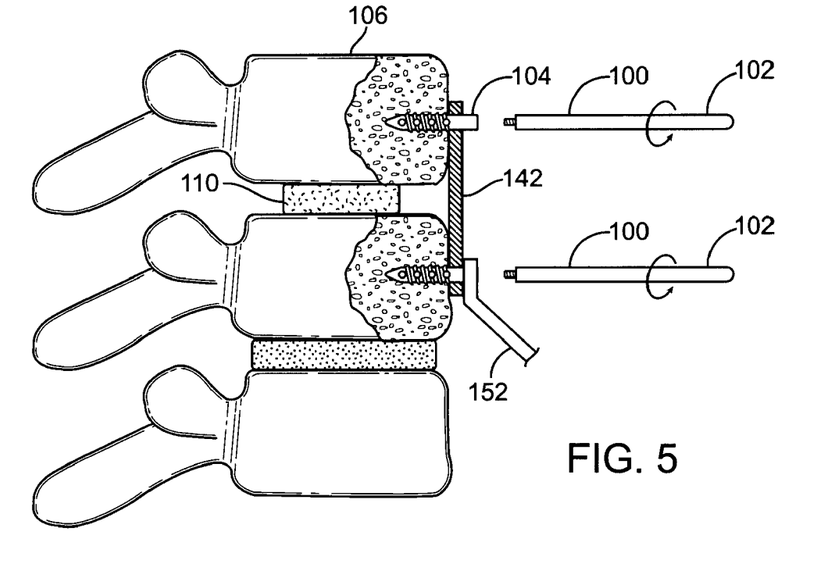
FIG. 5 shows the shaft section of the distraction pins being removed, leaving the screw sections of the pins still in the bone.

FIG. 5 shows the shafts 102 of the distraction pins 100 being removed after the plate 142 is in position, leaving the screw section 104 in place. It is important to note that in alternate embodiments, the shaft 102 could be removed prior to positioning the plate 142 over the screw section 104, while still maintaining many of the advantages of the invention previously described. In some embodiments it may be desirable to use a tool to grip or engage the screw section to prevent movement while the shaft is removed. In the embodiment seen in FIG. 5, a tool 152 prevents screw section 104 from rotating while the shaft 102 is unscrewed from the head 124 of screw section 104. Many tools 152 may be useable including but not limited to pliers and wrenches. In some embodiments, the screw section 104 may include features to enhance gripping by the tool 152 such as flats, texture, or apertures engaged by tool 152.

As previously discussed, in typical current procedures, empty bone holes created by removal of the distraction pins can interfere with proper placement of the bone screws used to anchor the plate and may lead to poor plate alignment along the long axis of the spine. Leaving the screw section 104 in place also reduces the bleeding that occurs when the distraction pins are removed in typical pre-existing procedures.

The plate 142 used in embodiments of the invention can be virtually any acceptable practical shape, and may be fabricated from any acceptable biologically compatible material or materials having sufficient strength for the intended use including but not limited to stainless steel, titanium, various alloys and plastics, some resins, and ceramics. The plate 142 may also include biologically active coatings that provide desired benefits such as enhancing bone growth or the like.

Figures 6A, 6B:
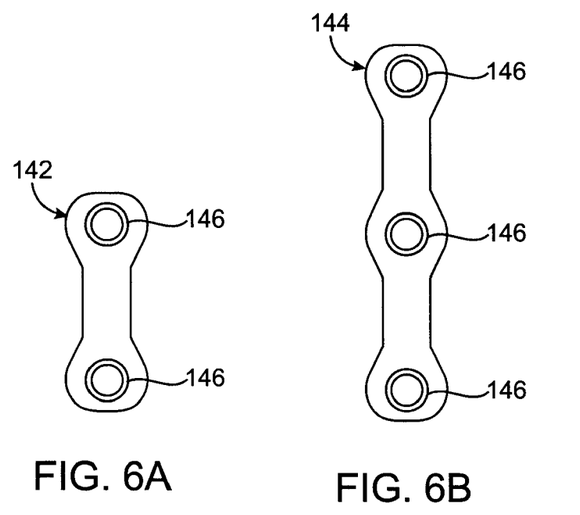
FIGS. 6a through 6d show several example plate embodiments.
Figure 6C:
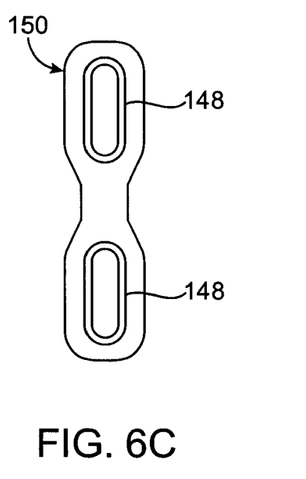
Figure 6D:
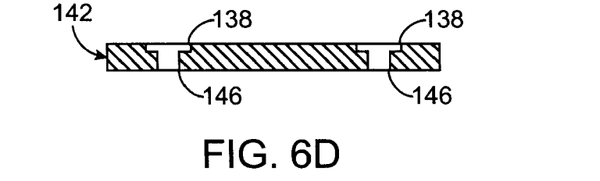

Example plate embodiments can be seen in FIGS. 6a through 6d. These are provided merely as examples and many other plate configurations may be used. FIG. 6a shows an example plate with for spanning two vertebrae, with one hole per vertebra. FIG. 6b shows an example plate 144 for spanning three vertebrae, also with one hole 146 per vertebra. The holes 146 of plates 142 and 144 are sized to snugly fit the screw section 104, so that there is little or no movement between the plate (142 or 144) and screw section 104. FIG. 6c shows an example dynamic plate 150 which has elongate holes 148 to allow some motion along the central axis of the spine, dynamic plates 150 are used to allow some subsidence as the bones mend. FIG. 6d shows a side view of the example plate 142 of FIG. 6a. The holes 146 may be counter sunk 138 so that the tops of locking screws inserted therein (which will be described later) will not protrude unacceptably far from the surface of the plate 142.

The embodiments shown in the Figures generally use plates having just one screw hole per vertebra, however, in other embodiments additional screw holes may be provided. In some plate embodiments having more than two screw holes per vertebrae, attachment to the screw sections of the distraction pins holds the plate in proper position while the additional screws are inserted in the additional holes. In other embodiments, more than two distraction pins may be used, and the plate is simply slid into position over all of the pins.

Figure 7:
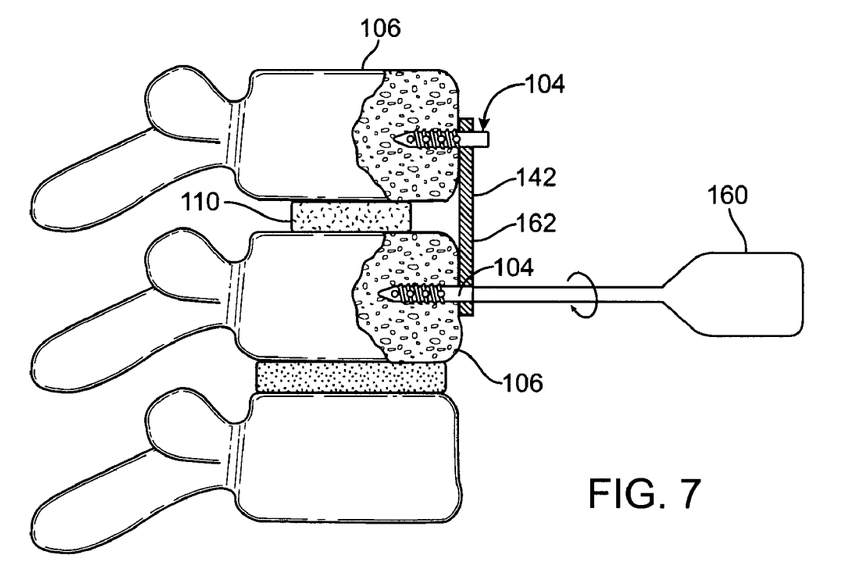
FIG. 7 shows the screw sections of the distraction pins being driven further into the bone.

Referring now to FIG. 7, once the plate 142 is in position, in some preferred embodiments, the screws 104 are then driven further into the bone. In FIG. 7 the top screw section 104 has not yet been driven further into the bone, and the bottom screw section 104 is being driven further into the bone with a screwdriver 160. Forces applied to the distraction pins 100 when used to move and position the vertebrae can cause the screws 104 to loosen. If nothing is done, then the plate 142 attached to the screws 104 may be able to shift, which may not be desirable. By driving the screws 104 further into the bone after the plate 142 is installed, the screws 104 gains fresh purchase on the bone, which may prevent any unwanted shifting that might otherwise have resulted. The screws 104 are driven a selected additional distance into the bone. In preferred embodiments, the top of the head 124 of the screw section 104 will be below the front surface 162 of the plate 142. In alternate embodiments, the top of the head 124 of the screw section 104 will be flush with the front surface 162 of the plate 142. In still other embodiments, the head 124 of the screw section 104 may be slightly higher than the front surface 162 of the plate 142.

Driving the screws 104 further into the bone after removal of the shafts 102 of the distraction pins 100 can be accomplished using any tool configured for the purpose, such as the screw driver seen in FIG. 7. In alternate embodiments, the shafts 102 of the distraction pins 100 may be rotated to drive the screws 104 deeper into the bone before removal.

Figure 8A:
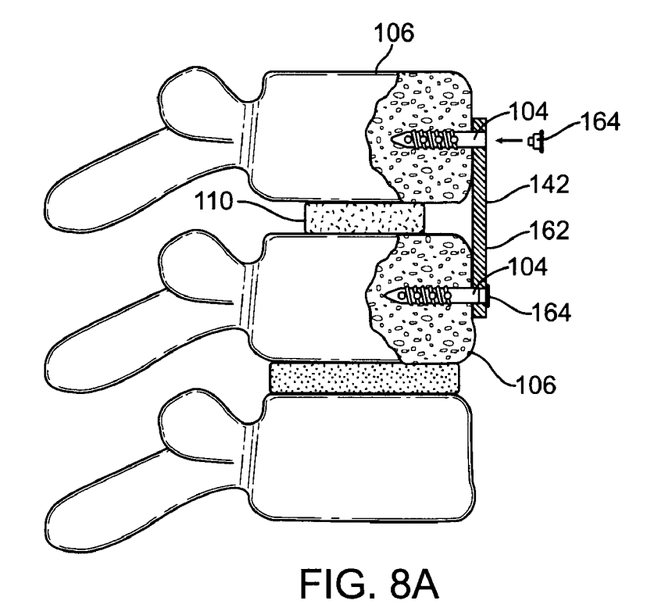
FIG. 8a through 8c shows the example locking screws being coupled to the screw section of the distraction pins, and details of the locking screws.
Figure 8B:
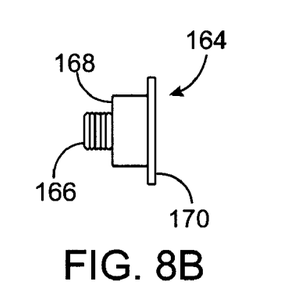
Figure 8C:
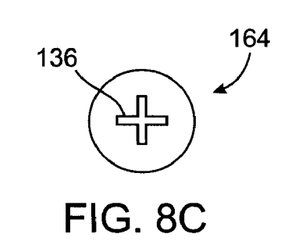

Once the screws 104 have been driven further into the bone, a locking screw is installed as seen in FIG. 8. The example locking screw 164 embodiment seen in FIG. 8b includes a threaded portion 166 for engaging the head 124 of the screw section 104, and a nonthreaded shoulder 168 for engaging the plate 142. The flange 170 is larger than the hole in the plate 142 in which the locking screw 164 is inserted, and assists in anchoring the plate 142. In some embodiments the plate may include a countersink to accept the flange so that a top of the locking screw is even with the surface of the plate 142. In this embodiment both the head 124 of the screw section 104 and the shoulder 168 of the locking screw 164 do not have threads. This configuration can be used for both static and dynamic plate installations. A dynamic coupling allows some motion between the plate and the screw. FIG. 8c shows a top view of the example locking screw 164 embodiment of FIGS. 8a and 8b. A cross shaped recess 136 is provided to engage the end of a Phillips head screwdriver. However, many other configurations could be used, including but not limited to a simple slot, or hex shaped recess.

Figure 9A:
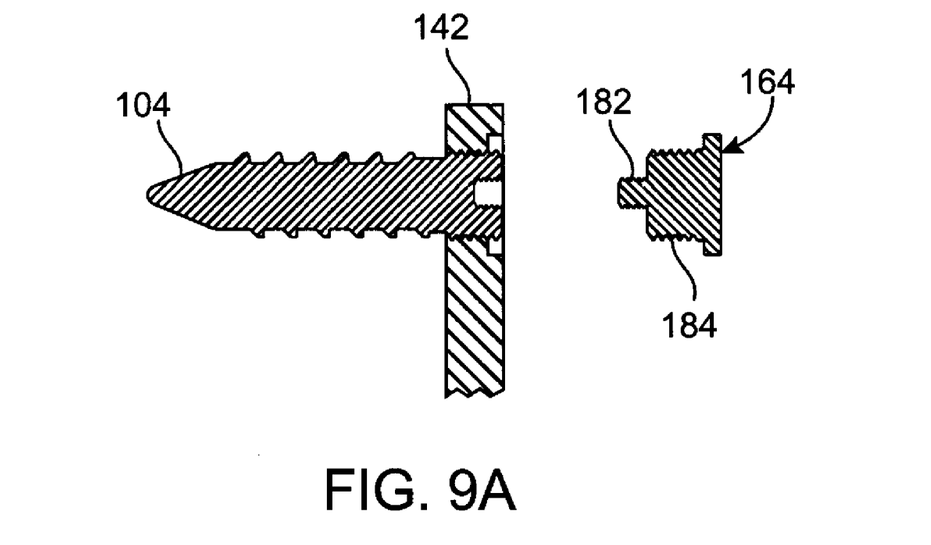
FIGS. 9a and 9b show additional screw section and locking screw embodiments.
Figure 9B:
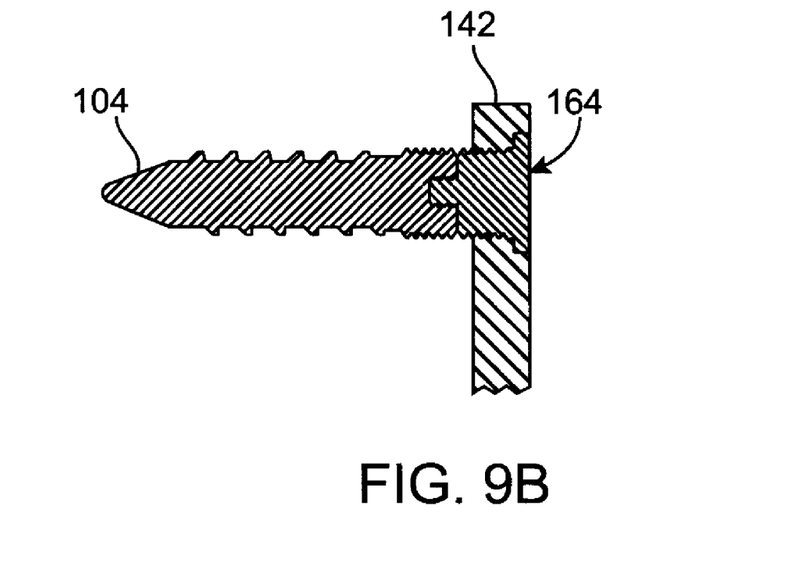

FIGS. 9a and 9b show details of alternate example embodiments of the locking screw. In this embodiment, the locking screw 164 includes a first threaded shank 182 to engage the head 124 of the screw 104, and a threaded shoulder 184 to engage the plate 142. In some embodiments the distraction screw may have threads on the head of the screw so that both the screw and the locking cap are threadably coupled to the plate. In other embodiments, only the locking screw is threadably coupled to the screw. FIG. 9b shows the locking screw 184 coupled to the plate 142 and screw section 104.

In both embodiments, the threaded shank 166 or 182 of the locking screw 164 or 180 may be made slightly larger than the aperture in the head 124 of the screw 104 configured to receive the threaded shank 166 or 182. When the locking screw 164 or 180 is threaded into the head 124 of the screw section 104, the head 124 is splayed out by the slightly larger shank, causing a very tight fit which inhibits the locking screw from backing out.

It will be understood that the forgoing is only illustrative of the principles of the invention, and that various modifications can be made by those skilled in the art without departing from the scope and spirit of the invention.

What is claimed is:

1. A method comprising the steps:
   placing a first distraction pin in a first bone, said first distraction pin having an upper section and a screw section;
   placing a second distraction pin in a second bone, said second distraction pin having an upper section and a screw section;
   acting on said distraction pins to position said first and second bones;
   sliding a plate over said distraction pins;
   following sliding said plate over said distraction pins, driving said first and second screw sections further into said first and second bones,
   removing said upper portion of said distraction pins;
   connecting a locking element to each said screw section of said first and second distraction pins;
   whereby said plate is held in position by said locking elements and said screw sections of said distraction pin.

2. The methods of claim 1 wherein said screw sections are driven into said bone until a top of said screw sections is flush with a front surface of said plate.

3. The methods of claim 2 wherein said screw sections are driven into said bone until a top of said screw sections is below a front surface of said plate.

4. A method comprising the steps:
   placing a first distraction pin in a first vertebral body, said first distraction pin having an upper section and a screw section;
   placing a second distraction pin in a second vertebral body, said second distraction pin having an upper section and a screw section;
   acting on said distraction pins to position said first and second vertebrae;
   removing said upper portion of said distraction pins;
   sliding a plate over a head of said screw section of said distraction pins;

following sliding said plate over said head of said screw portion of said distraction pins, driving said first and second screw sections further into said first and second bones;

connecting a locking element to each said screw section of said distraction pin; whereby said plate is held in position by said locking element and said screw section of said distraction pin.

* * * * *